United States Patent [19]

Inbasekaran

[11] Patent Number: 5,470,987
[45] Date of Patent: Nov. 28, 1995

[54] BISIMIDE MONOMERS

[75] Inventor: Muthiah N. Inbasekaran, Midland, Mich.

[73] Assignee: The Dow Chemical Company, Midland, Mich.

[21] Appl. No.: 315,054

[22] Filed: Sep. 29, 1994

Related U.S. Application Data

[62] Division of Ser. No. 161,969, Dec. 3, 1993, Pat. No. 5,386,002.

[51] Int. Cl.⁶ .................................................... C07D 403/10
[52] U.S. Cl. ........................................................... 548/462
[58] Field of Search ............................................ 548/462

[56] References Cited

U.S. PATENT DOCUMENTS

| | | | |
|---|---|---|---|
| Re. 29,316 | 7/1977 | Bargain et al. | 260/30.2 |
| 3,380,964 | 4/1968 | Grundschober et al. | 260/47 |
| 3,730,946 | 5/1973 | Heath et al. | 260/47 R |
| 3,968,083 | 7/1976 | Quinn | 260/47 |
| 4,005,134 | 1/1977 | Markezich | 260/520 |
| 4,297,474 | 10/1981 | Williams et al. | 528/170 |
| 4,499,165 | 2/1985 | Molaire | 430/17 |
| 4,584,258 | 4/1986 | Detty et al. | 430/270 |
| 4,732,963 | 3/1988 | Wank | 528/205 |
| 5,082,920 | 1/1992 | Harper | 528/205 |
| 5,104,960 | 4/1992 | Inbasekaran et al. | 528/125 |
| 5,171,820 | 12/1992 | Mang et al. | 528/125 |
| 5,340,904 | 8/1994 | Yang et al. | 528/185 |

OTHER PUBLICATIONS

Chin–Ping Yang, "Preparation and properties of cardo poly(amine–imide)s derived from 9,9–bis(4–aminophenyl)fluorene, trimellitic anhydride, and various aromatic diamines," *Makromol Chem*, vol. 193, pp. 445–453(1992).

J. K. Stille, "Polyquinolines Containing Fluorene and Anthrone Cardo Units: Synthesis and Properties," *Macromolecules*, vol. 14, pp. 486–493(1981).

K. L. Mittal, "Polyetherimide: A Versatile, Processable Thermoplastic," *Polymides*, vol. 1, Plenum Press, New York and London, pp. 149–161(1984).

R. W. Lenz, *Organic Chemistry of Synthetic High Polymers*, John Wiley & Sons, pp. 82–95, (1967).

V. V. Rode et al., "Effect of Amide Bonds on the Thermal Stability of Polyimides," *Vysokomolekulyarnye Soedineniya*, Ser. A, 12(7), 1566–1573(1970).

*Primary Examiner*—Jacqueline Haley
*Attorney, Agent, or Firm*—J. B. Treangen

[57] ABSTRACT

Monomeric bisimides corresponding to the formula:

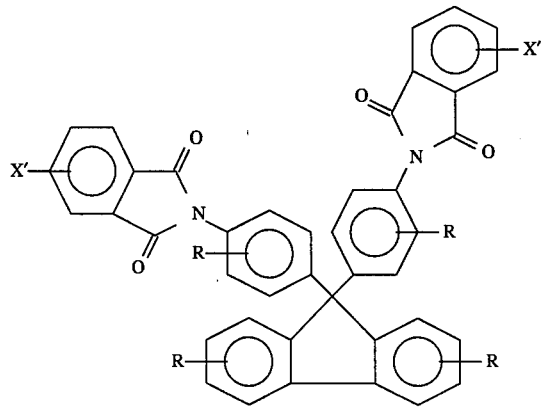

wherein R is independently in each occurrence hydrogen, alkyl of from 1 to 20 carbons, aralkyl of from 1 to 20 carbons, halogen, or $NO_2$; X' is F, Cl, OH, or $NO_2$. These bisimides are useful in the production of various thermoplastic, polymeric materials such as polyetherimides, polyesterimides, and poly(carbonate imides).

6 Claims, No Drawings

BISIMIDE MONOMERS

This application is a division of application Ser. No. 08/161,969, filed Dec. 3, 1993 now U.S. Pat. No. 5,386,002 (incorporated herein by reference).

BACKGROUND OF INVENTION

This invention relates to bisimides.

Bisimides and polyetherimides derived therefrom are known. For example, Serfaty reports in *Polyimides: Synthesis, Characterization, and Applications,* Volume 1 (1984) at page 149 that polyetherimide was a resin introduced commercially in 1982. This polyetherimide was made from bis{1,3-(4-nitrophthalimido)}benzene and bisphenol A. This polyetherimide is a thermoplastic which has been used in electrical, electronics, transportation, and appliance applications. More recently, Yang et al. reported in *Makromol. Chem.,* volume 193, pages 445–453 (1992), the preparation of cardo poly(amide-imide)s derived from 9,9-bis(4-aminophenyl)fluorene, trimellitic anhydride, and various aromatic diamines. However, this disclosure is limited to a specific fluorene derivative and to specific polyamides derived therefrom, Current research efforts have been directed at finding new aromatic bisimides and polymers made therefrom.

SUMMARY OF INVENTION

This invention is a bisimide of the formula (hereinafter referred to as "Formula II"):

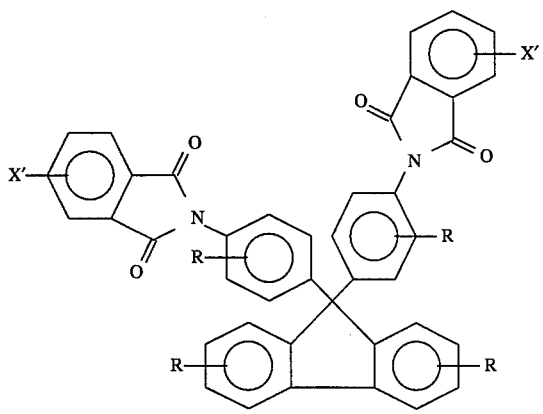

wherein R is independently hydrogen, alkyl of from 1 to 20 carbons, aryl or aralkyl of from 1 to 20 carbons, halogen, or $NO_2$; and X' is F, Cl, OH, or $NO_2$.

Bisimides of this formula are useful, for example, as monomers in the production of various thermoplastic, polymeric materials. The polymeric materials are useful in the production of such things as films, coatings, and as injection moldable plastics.

DETAILED DESCRIPTION OF THE INVENTION

Copending patent application Ser. No. 08/161,969 (filed Dec. 3, 1993), is directed to thermoplastic, polymeric material containing a repeating unit corresponding to the following Formula I:

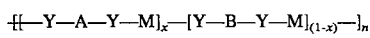

wherein A is a bisimide of Formula IIA:

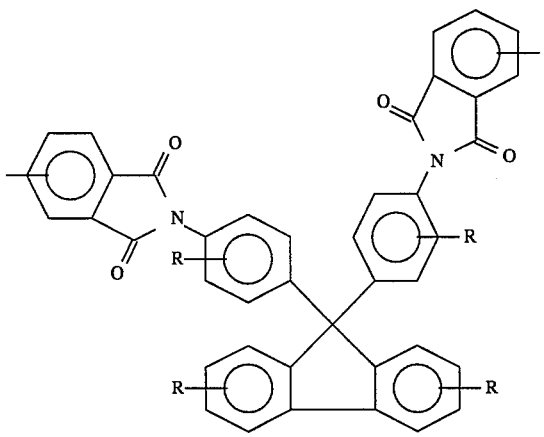

wherein R is independently in each occurrence hydrogen, alkyl of from 1 to 20 carbons, aryl or aralkyl of from 1 to 20 carbons, halogen, or $NO_2$; x is from about 0.1 to 1; n is from about 5 to about 1000; Y is independently in each occurrence a covalent bond or CO; B is independently in each occurrence a divalent hydrocarbylene moiety optionally substituted with halogen, alkyl, aryl, aralkyl, wherein the entire divalent hydrocarbylene moiety contains from 1 to 50 carbons; or wherein B is a divalent moiety of Formula III:

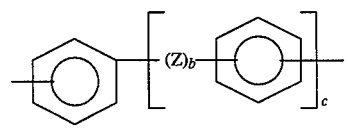

wherein Z is $CH_2$, $CH_2CH_2$, $C(CH_3)_2$, $CF_2$, $C(CF_3)_2$, $OCH_2O$, $OCH_2CH_2O$, $CO_3$, O, S, SO, $SO_2$, $SO_3$; b is 0 or 1; and c is 0, 1, or 2; wherein M is independently in each occurrence —O—B—O—, —O—CH$_2$CHOHCH$_2$—O—B—O—CH$_2$CHOHCH$_2$—O—, —O—CH$_2$CHOHCH$_2$—O—, —O—CO—O—, or —O—CO—B—CO—O— with the proviso that M is not —O—CO—O— or —O—CO—B—CO—O— when Y is —CO—.

The aromatic bisimides of this invention are useful as monomers for production of thermoplastic, polymeric material in the practice of the aforementioned copending patent application. Preferably, X' is F when the bisimide is used to make polyetherimides and X' is OH when the bisimide is used to make polycarbonateimides and poly(carbonate ester imides).

For each of Formulas II and IIA, when R is alkyl, the alkyl group can be linear, branched, or cyclic. Exemplary of aryl or aralkyl R groups include phenyl, biphenyl, naphthyl, benzyl, methylphenyl. R is preferably independently in each occurrence hydrogen or alkyl of from 1 to 6 carbons; most preferably, R is hydrogen in each occurrence for each of Formulas II and IIA.

The novel aromatic bisimides of Formula II are useful as monomers as described herein. In Formula II, X' is preferably F or OH.

In Formula I of the aforementioned copending patent application, a polyetherimide is a material wherein Y is a covalent bond and M is —O—B—O—. Units of Formula I correspond to the residue of monomeric aromatic bisimides of Formula II. In Formula I, x is preferably in the range of 0.25 to 0.75.

The preferred divalent hydrocarbylene moieties of B in Formula I include divalent aromatic moieties such as arylene, alkylenearylene, dialkylenearylene, diaryleneketone, diarylenesulfone, diarylenesulfoxide, alkylidene-diarylene, diarylene oxide, diarylene sulfide, diarlyenecyanomethane or divalent aliphatic moieties such as alkylene, alkylene oxide, alkylene sulfide, alkylene sulfoxide, or the like. More preferred divalent moieties include 1,3-phenylene, 1,4-phenylene, biphenylene, napthylene, isopropylidenediphenylene, methylenediphenylene, oxydiphenylene, diphenylene sulfide and diphenylene sulfoxide. More preferred moieties include 1,3-phenylene, 1,4-phenylene, biphenylene, napthylene and isopropylidenediphenylene. In Formula III, Z is preferably $CH_2$, $CH_2CH_2$, $C(CH_3)_2$, $CF_2$, $C(CF_3)_2$, $OCH_2CH_2O$ or O; more preferably Z is O.

The aromatic bisimides are prepared generally by condensing 9,9-bis(4-aminophenyl)fluorene substituted such that a final aromatic bisimide of Formula II is provided with a phthalic anhydride substituted by X' in accordance with Formula II. The substituted 9,9-bis(4-aminophenyl)fluorene compound can be prepared according to the procedure of Stille et al., *Macromolecules*, volume 14, 486 (1981). The phthalic anhydrides useful in the practice of this invention are readily made by well known methods and are readily available commercially. The general reaction conditions for the condensation of the substituted 9,9-bis(4-aminophenyl)fluorene and the phthalic anhydride are as follows. From about 2 to about 4 equivalents, preferably from about 2 to about 2.6 equivalents, and most preferably from about 2.1 to about 2.2 equivalents of the phthalic anhydride and one equivalent of the unsubstituted or substituted 9,9-bis(4-aminophenyl)fluorene are combined in a dipolar aprotic solvent such as dimethylformamide (DMF), dimethylsulfoxide (DMSO), N-methylpyrrolidine (NMP), acetic acid and m-cresol. The condensation reaction is run at a temperature typically greater than or equal to about 20° C. preferably greater than or equal to about 50° C., more preferably greater than or equal to about 120° C.; typically less than or equal to about 200° C., preferably less than or equal to about 170° C. and more preferably less than or equal to about 160° C. Pressure can be atmospheric, superatmospheric or subatmospheric. The condensation reaction is carried out for from about 10 minutes to about 100 hours, depending on the amount of reactants, temperature, solvent, pressure and the like. The aromatic bisimides produced from the condensation reaction are recovered using well known techniques such as filtration and distillation and likewise purified by well known techniques such as distillation, washing with an organic solvent, recrystallization and chromatography. In the case where X' is hydroxy, the bisimide can be prepared by reacting 2 to 3 molar equivalents of the 4-hydroxyphthalic acid with one molar equivalent of 9,9-bis(4-aminophenyl)fluorene in refluxing acetic acid.

The techniques used to produce polyetherimides are well known in the art. See, for example, U.S. Pat. No. 4,297,474. Typically, in the practice of this invention, a substituted aromatic bisimide is reacted with an alkali metal phenate to form the polyetherimide. The alkali metal phenate can be either monocyclic or polycyclic and contain two phenate groups. The phenates are reacted to yield polymeric materials as described above containing an —O—B—O— group wherein this group is a phenate residue. Group B when of Formula III thus corresponds to materials derived from phenates. Suitable phenols from which the phenates can be derived are of Formula IIIA:

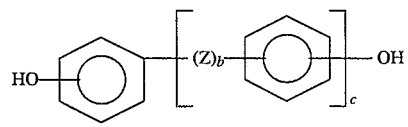

wherein Z, b and c are as described above. Examples of suitable phenols from which the phenates are derived include 2,2-bis(4-hydroxyphenyl) propane, 4,4'-dihydroxy diphenyl oxide, 4,4'-dihydroxydiphenyl sulfide, 4,4'-dihydroxydiphenyl sulfoxide, 1,1,1,3,3,3,-hexafluoro- 2,2-bis(4-hydroxyphenyl)propane, 4,4'-dihydroxydiphenyl methane, 1,4-benzenediol, and 1,3-benzenediol. The alkali metal phenate can be added directly or formed by reaction of an alkali metal salt such as sodium or potassium bicarbonate with a phenol. In the polymerization of the alkali metal phenate with the substituted aromatic bisimide, a solvent can be used such as dimethyl-acetamide, dimethylformamide, N-methylpyrrolidone, and diglyme. After polymerization of the reactants, the polyetherimide is recovered and purified by well known methods. Alternatively, the polyetherimides can also be prepared by reacting the fluoro-substituted bisimide with the trimethylsilyl derivative of the bisphenol in the presence of a catalyst such as an alkali metal fluoride, preferably cesium fluoride, in an aprotic organic solvent such as diphenyl sulfone. See, in this regard, H. R. Kricheldorf et al., *J. of Polymer Science: Polymer Chemistry Ed.*, volume 21, pages 2283–2289, (1983).

The polymeric materials of the aforementioned copending patent application can be used to make films, coatings and as injection moldable plastics to make mold parts, for example. The polymeric materials of the aforementioned copending patent application can be reinforced with a variety of particulated fillers such as glass fibers, silica fillers and carbon whiskers. The particulated fillers can be added to the polymeric materials prior to polymer formulation by effecting polymerization in the presence of filler. Melt blending and solution blending can also be used to add the particulated fillers to the polymeric materials of the aforementioned copending patent application.

The polymers of the aforementioned copending patent application are processible as thermoplastics. A thermoplastic is defined as a material which flows at temperatures above its glass transition temperature and in which crosslinking or network formation does not occur. Thermoplastic processing is defined as heating a material to a temperature sufficient for flow to occur, with subsequent or concurrent forming into a shaped article. The article can be reheated and reformed any desired number of times, and the polymer does not undergo crosslinking or network formation during this handling. A test for crosslinking can be made by attempting to dissolve the material in a solvent, especially after exposure to the temperatures encountered during thermoplastic processing. Crosslinked materials will not dissolve, while uncrosslinked materials will dissolve. Thermoplastics may be extruded at temperatures above their glass transition temperatures or they can be compression molded into films and plaques, and they remain both soluble and processible after such thermal treatment.

The following examples are given to illustrate the invention and should not be interpreted as limiting it in any way. Unless stated otherwise, all parts and percentages are given by weight.

EXAMPLE 1

Preparation of Several Bisimides 9,9-Bis{4-(4-fluorophthalimido)phenyl}fluorene A mixture of 9,9-bis(4-aminophenyl)fluorene (17.4 g, 50 mmol), 4-fluorophthalic anhydride (18.3 g, 110 mmol), and 250 ml of acetic acid was stirred and heated under reflux for five hours and then stirred at ambient temperature overnight. A colorless precipitate formed which was filtered, washed twice with 150 ml of ethanol, washed twice with 100 ml of hexane, suction-dried for two hours, and then dried in a vacuum oven at 120° C. for 16 hours. The title compound was isolated as a colorless powder (29.2 g, 90.6% yield) that had melting point of 323.5°–326° C. and a $^1$H NMR spectrum (DMSO-$d_6$) corresponding to δ8.02 (m, 4H), 7.86 (dd, 2H), 7.72 (m, 2H), 7.60 (d, 2H), 7.46 (t, 2H), and 7.35 (m, 10H).

9,9-Bis {4 -(4-hydroxyphthalimido)phenyl}fluorene

A mixture of 4-hydroxyphthalic acid (4.0 g, 22 mmol), 9,9-bis(4-aminophenyl)fluorene (3.5 g, 10 mmol), and 40 ml of acetic acid was stirred and heated under reflux for 48 hours. After cooling to room temperature, the precipitate was collected by filtration and washed with acetic acid (2×25 ml) to provide the title compound as a colorless powder having a melting point greater than 300° C. (3.4 g, 53.1% yield). The nuclear magnetic resonance and infrared spectrum were consistent with the structure.

9,9-Bis{4-(4-nitrophthalimido)phenyl}fluorene

A mixture of 9,9-bis(4-aminophenyl)fluorene (3.5 g, 10 mmol) and 40 ml of acetic acid was stirred and then 4-nitrophthalic anhydride (4.1 g, 21 mmol) was added to the mixture. The resulting mixture was stirred and heated under reflux for 7 hours. After cooling, the beige-colored precipitate was filtered, washed with acetic acid (2×100 ml) and then with water (500 ml). The washed precipitate was recrystallized from dimethylformamide-methanol to provide the title compound as an off-white powder (5.1 g, 73% yield) having a melting point of 360°–363° C.

EXAMPLE 2

Preparation of a Polyetherimide from 9,9-Bis(4-(fluorophthalimido)phenyl)fluorene and Bisphenol A A 250 ml flask was charged with 9,9-bis(4-(fluorophthalimido)phenyl)fluorene (19.34 g, 30 mmol), bisphenol A (6.85 g, 30 mmol), potassium carbonate (18.65 g, 135 mmol), 90 ml of dimethylacetamide, and 60 ml of toluene. The mixture was stirred under a continuous nitrogen purge and heated to 100° C. for 30 minutes and then to 135° C. for 90 hours. The viscous solution was poured into 2 liters of methanol and the resulting solid was then slurried with 200 ml of methylene chloride, then with water. The off white solid was filtered and dried in a vacuum oven at 150° C. for 16 hours. $T_g$ was not detectable by Differential Scanning Calorimetry. The solid had an inherent viscosity of 0.54 dL/g measured in dimethylacetamide at 25° C. at a concentration of 0.5 g/dL. The $^1$H and $^{13}$C NMR spectra ($D_6$ DMSO) were consistent with the assigned structure.

EXAMPLE 3

Preparation of a Polyetherimide from 9,9-Bis(4-(fluorophthalimido)phenyl)fluorene and Trimethylsilylated Bisphenol A A 300 ml resin kettle was charged with 9,9-bis(4-fluorophthalimido)phenyl)fluorene (19.34 g, 30 mmol), 2,2-bis(4,4'-trimethylsiloxyphenyl)propane (10.90 g, 29 mmol), diphenyl sulfone (10 g), and chlorobenzene (25 ml). The mixture was stirred under a continuous nitrogen purge and heated to 335° C. After the chlorobenzene distillate was collected, approximately 2 mg of cesium fluoride was added to the resin kettle. Immediately after addition of the cesium fluoride catalyst, a liquid rapidly distilled from the solution. The reaction was stirred for 20 minutes and the reactor was removed from the heating bath. The polymer was then slurried with 200 ml of dimethylacetamide. The dimethylacetamide soluble portion was precipitated into 2 liters of methanol and the resulting solid dried in a vacuum oven at 150° C. for 16 hours. $T_g$ was 262° C. at 10° C./minute. The dry solid weighed 23.1 g (92.5% yield). A compression molded film of the dry polymer of 20 mils thickness molded at 330° C. was brittle. The inherent viscosity of the polymer was 0.22 dL/g measured in dimethylacetamide at 25° C. at a concentration of 0.5 g/dL.

What is claimed is:

1. A bisimide of the formula:

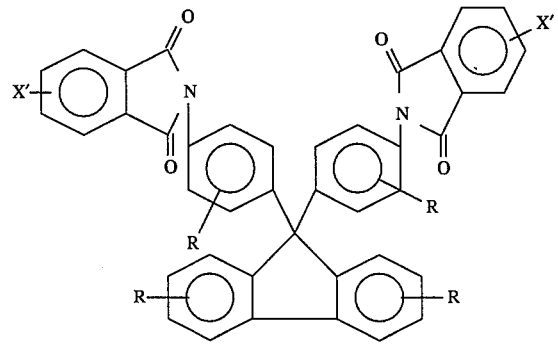

wherein R is independently in each occurrence hydrogen, alkyl of from 1 to 20 carbons, aralkyl of from 1 to 20 carbons, halogen, or $NO_2$; X' is F, Cl, OH, or $NO_2$.

2. The bisimide of claim 1 wherein R is independently in each occurrence hydrogen or alkyl of from 1 to 6 carbons.

3. The bisimide of claim 1 wherein R is hydrogen in each occurrence.

4. The bisimide of claim 3 wherein X' is F.

5. The bisimide of claim 3 wherein X' is Cl.

6. The bisimide of claim 3 wherein X' is OH.

* * * * *